United States Patent [19]
Yancey

[11] Patent Number: 5,329,322
[45] Date of Patent: Jul. 12, 1994

[54] PALM SIZE AUTOREFRACTOR AND FUNDUS TOPOGRAPHICAL MAPPING INSTRUMENT

[76] Inventor: Don R. Yancey, P.O. Box 362, Hilo, Hi. 96721

[21] Appl. No.: 888,166

[22] Filed: May 26, 1992

[51] Int. Cl.$^5$ ............................ A61B 3/10; A61B 3/00
[52] U.S. Cl. ..................................... 351/211; 351/221; 351/246
[58] Field of Search ................. 351/211, 214, 246, 221

[56] References Cited

U.S. PATENT DOCUMENTS 5,157,427 10/1992 Humphrey .......................... 351/211

Primary Examiner—Scott J. Sugarman
Assistant Examiner—Darryl J. Collins
Attorney, Agent, or Firm—Brown, Martin, Haller & McClain

[57] ABSTRACT

A schematic is disclosed for an optical instrument with a compact light path for incorporation to a hand held instrument for objective refraction of the eye. In particular, and after eye centering occurs, utilizing an eye examiner to patient sight path and an automated indication of centering using conventional Purkinje images, first and second light sources electronically bracket the patient's gross sphere. Thereafter, a light source array is registered on one or the other side of the determined gross sphere prescription and analyzed for astigmatism. There results a rapid objective refraction particularly useful with children whose limited attention span renders the use of more conventional autorefractors not practicable.

14 Claims, 6 Drawing Sheets

PALM SIZE AUTOREFRACTOR AND FUNDUS TOPOGRAPHICAL MAPPING INSTRUMENT

A schematic is disclosed for an optical instrument with a compact light path for incorporation to a palm-size instrument for objective refraction of the eye. In particular, and after eye centering occurs, a light source image array is registered on one or the other side of the determined gross sphere prescription and analyzed for refractive error. There results a rapid objective refraction particularly useful with children whose limited attention span renders the use of more conventional autorefractors not practicable. Provision is made for determining precise eye centering as well as topographical mapping of the eye.

BACKGROUND OF THE INVENTION

Measuring the refraction of the eye is difficult as the eye is a living organ and is constantly changing and moving. Even with an intelligent and cooperative patient fixating a target, the eye will be moving because of micronystagmus. Without this constant motion, the eye cannot function. It is an established phenomenon that the eye is a differential sensing mechanism; if an image is perfectly fixed on the retina, the brain causes the image to fade from view. To view, the eye must be constantly moving.

Alignment is a major problem for most methods of refraction. The optical axis of the eye must match the optical axis of the measuring instrument. Several methods of eye alignment have been used in the prior art.

One method to help ensure proper eye alignment is TV imaging. Typically such TV imaging enlarges the eye many times so the examiner can determine that the eye is properly fixated and hopefully aligned.

A second method uses an eye tracker that follows the movement of the eye. Because of the double-pinhole principle used in most machines, alignment is critical.

In order to avoid the alignment problem, it has been known to use a measurement beam that over-fills the pupil so that alignment was not critical. The chief disadvantage of such instruments was the long measurement times (up to 20 seconds) have been required to measure each eye.

Because the eye is constantly changing, measurements taken at different times can show different values due to random effects. The longer time interval required for the measurement, the longer the integration of that measurement to previously obtained values so that random effects are averaged out to improve the signal-to-noise ratio and thereby improve accuracy. One way to avoid movement errors is to have a very short measurement time, say one millisecond. Unfortunately, random errors appear in these short measurements.

The above problems of the measurement of refraction are compounded in the case of children. Objective refraction of children has always been associated with problems. Children have wide powers of accommodation; this means that conventional testing may obtain various refractive readings. Further, children simply do not stay in the same place for overlong periods of time. Consequently, a different method of autorefraction is required. Finally, large and imposing optical apparatus—for example most conventional autorefractors—tend to excite and frighten the youthful subjects. This is especially true if the intimate presence of an operator proximate the child patient is required. Simply stated, the excited and frightened juvenile subject falsely accommodates—and the measurement of such refractions can be in error.

Accommodative error is the biggest problem in providing accurate and reproducible measurements. In order to see objects close-up, the lens of the eye must change shape, become "fatter" so that the nearby object will be clearly focused on the retina. Looking into a box, or any type of instrument, even when the object being viewed inside the box is at optical infinity induces accommodation. This is a psychological phenomenon. It has been discovered that when a subject looked through a small hole (such as a hole in a wall so that the subject thought he was looking into another room although the viewed object might be close by) caused accommodation to be relaxed.

Even older children—intelligent and trying to cooperate—because of lack of experience may not be able to readily position themselves in the chin/forehead rests, properly fixate the target, and remain still for the requisite measurement time. For infants and younger children refraction is even more difficult.

Bringing an instrument close to the child's eyes may cause the child to close his eyes and resist examination. In this case, measurement must be taken from a distance. One method of measuring from a distance of about one meter is using photorefraction techniques. Current instrumentation replaces photographic film with CCDs (charge-coupled devices) to get quick readouts.

No one has "solved" the problem of accommodation.

Three main methods used to relax accommodation (refraction is measured at optical infinity, "making" the eye change its optics to see a target at optical infinity) are the following: 1) having the patient fixate an object 5 meters or further away, 2) fixate a point of light or a "featureless" pattern, and 3) "fog" the eye with a positive lens so that accommodation causes the fixated target to become more blurred and thus encouraging relaxation of the accommodative mechanism.

The usual method to relax accommodation is using the fogging method. With a positive lens, the eye is refracted to get an initial reading. Then an in-focus target such as a sailboat on the ocean, a tractor in a field, or a balloon in the sky, is presented to the patient, which is fogged to relax accommodation and get the patient's refractive reading.

In cases of latent hyperopia in some children, fogging is not effective and a cycloplegia must be used to relax accommodation.

Another problem in providing accurate and reproducible refractions is that the basic meridional method of refraction requires great accuracy of the initial measurements. It can be mathematically shown that meridional error as little as one-quarter diopter can cause entirely erroneous results.

Meridional refraction requires a minimum of three meridional measurements, and these data are put into Lawrence's formula to calculate mean sphere, cylinder, and axis. If measurements are not accurate, as noted above, or if astigmatism is irregular, refraction can be in significant error. One approach to this problem is to search for the principal axes of astigmatism to provide better accuracy.

While the following disclosed instrument is particularly useful with children, it will be understood that the disclosed apparatus can be utilized with all segments of the eye patient population.

SUMMARY OF THE INVENTION

The optical path for a simple palm-size autorefractor suitable for the rapid refraction of children is disclosed. The instrument includes an operator to patient eye sight path for initial gross instrument alignment. Once gross instrument alignment occurs, first and second images are projected along the interrogating optical axis onto the fundus of the eye. These first and second images bracket the conventional prescription of an emmetrope by fixed diopter prescriptions (for example, bracketed by a $-20$ diopter image and a $+20$ diopter image). The light retro reflected from these images is received at discrete detectors for each projected image and compared differentially to determine gross spherical prescription. A circuit is disclosed to prevent pupil dilation from interfering with the described measurement. Thereafter, an emitter array with corresponding micro lens array projects to the eye—preferably on one identifiable side of the determined gross spherical prescription—to cover the central portion of the cornea with a preferably regular image array. A corresponding detector array with a corresponding micro lens array projects to a corresponding matrix on the eye and relays for detection the images of the projected emitter array to a detector. At the detector, the intensity of the received interrogating image matrix is received and compared. There results on the detector array telltale axial patterns co-incident to the principal axes of any astigmatic properties of the lens including axis and power information.

A precise instrument alignment protocol is disclosed. A Purkinje imaging system including a beam splitter operable in a discrete chromatic wave length (e.g. green) projects images along the interrogating optical axis of the instrument. The projected images are examined through a detector for coincidence between the reflected Purkinje images of the optical interfaces of the cornea and front and back eye lens surfaces. By the expedient of image registration at a monitoring detector coupled to a log amplifier for determining comparison of image intensity of all the respective Purkinje images, rapid indication of instrument alignment is signaled.

Thereafter, a scheme of retinal mapping of the eye fundus is disclosed. Provision can be made to focus the emitter array and detector array to the fundus for greater mapping resolution. An imaging system operable with only one moving part results which can effect a rapid mapping autorefraction.

OTHER OBJECTS, FEATURES AND ADVANTAGES

An object of this invention is to enable direct measurement of sphere. This measurement is obtained through precise measurement of line spread or blur. As a consequence power of the measured eye in plus or minus diopter for spherical measurement of the eye is directly obtained.

An advantage of the system is that it contains no moving parts. As a consequence, the system likewise does not contain critical optics.

A further object of the invention is to disclose an instrument that can measure the topological profile of the eye. According to this version of the instrument, the topological mapping version of the instrument has one step-wise moving part, this part usually constituting a moving light array or lens. When the instrument operates in the topological mapping mode, small apertures enable projection of small discs onto the retina of the eye to measure, when finely refracted, the topology of all discrete locations on the fundus.

A further advantage is that the one moving part which employs discrete lensed photodetectors can instead constitute a CCD in order to obtain high-resolution images of the fundus.

A further advantage of this invention is that the measurement beams overfills the pupil so that when the patient fixates the target, the eye is automatically self-aligned to relatively large limits.

Yet another advantage of the disclosed optical train is that the refracting instrument can use ordinary light emitting diodes (LEDs).

An additional advantage of this invention is that the entire area of lens in the pupil can be refracted by only a portion of the projected beams. As a consequence, the disclosed instrument can refract through a small pupil.

An object of this invention is to disclose a protocol for determining astigmatism compatible with the disclosed optics. Accordingly, astigmatism is determined by "elliptical" deformation of a projected circular disc. Axis and cylinder can be calculated with Lawrence's formula or by curve fitting or by measuring the astigmatic blur circle's orientation and ratio of length-to-width using a simple look-up table. This third method is particularly applicable to an instrument that uses CCDs in place of the $-$diopter and $+$diopter photodiodes.

With a fixed photodetector array, the meridians of the array correlate to astigmatism. In the step-wise movable lens or emitter/photodetector array, the meridians of the topological map corresponding to measured astigmatism.

Accordingly, and so that the array may be compact and sufficiently sensitive to record various signal levels, emitters/photodetectors are lensed using a microlens array (fabricated from a single sheet of photosensitive glass using UV techniques), and emitters can be low-intensity microlasers.

A further advantage of this invention is that a very wide diopter range can be measured, from $-20$ to $+20$ diopters.

An additional object of this invention is to disclose a refractor without moving parts which can incorporate pulsating light sources. Accordingly, the use of pulsating LEDs is utilized. This results in an instrument that can make many measurements per second, (rates ranging to 100 pps or more), using pulse techniques that enable miniaturized components of low average power to produce high peak optical outputs.

A further advantage of the disclosed electronic protocol is that a Purkinje imaging system can be used to screen the desired optical measurement. The Purkinje system signals that the instrument is in alignment for taking of accurate refraction measurements. When this alignment is detected, signal processing of the received refraction values eliminates spurious measurements, averages into the final refraction only those measurements taken where the patient is actually fixating with his eye aligned and not accommodating for the desired measurement.

A further object of this invention is to disclose electronics and optics in combination that indicate when the eye is in place, aligned, and not accommodating.

An additional object of this invention is to disclose techniques and circuits to compensate for changes in eye conditions (such as changing pupil size, etc.) in order to normalize the eye and ensure accurate and reproducible refractions.

A further object of this invention is to set forth protocols for instrument autocalibration for extreme linearity and long term zero-drift stability.

Yet an additional advantage of this invention is to disclose an electronic circuit from which data can be extracted to detect amblyopia.

DESCRIPTION OF THE PREFERRED EMBODIMENT

Figure 1:
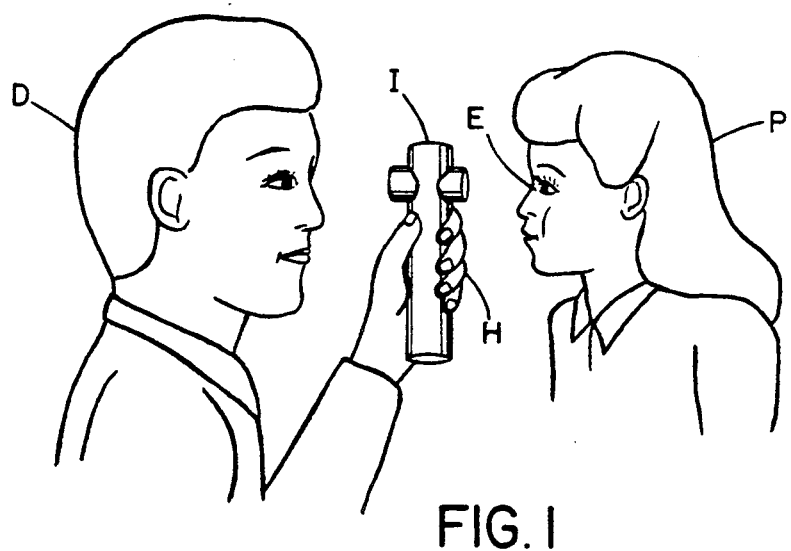
FIG. 1 is a perspective view of a child with an eye examiner holding the hand held instrument of this invention to the eye of a child for autorefraction of the child patient's prescription.

Referring to FIG. 1, an eye examiner D is shown holding instrument I of this invention to eye E of patient P. As can be seen, instrument I is of a hand held variety and is held in hand H of eye examiner D during the objective refraction.

Figure 2:
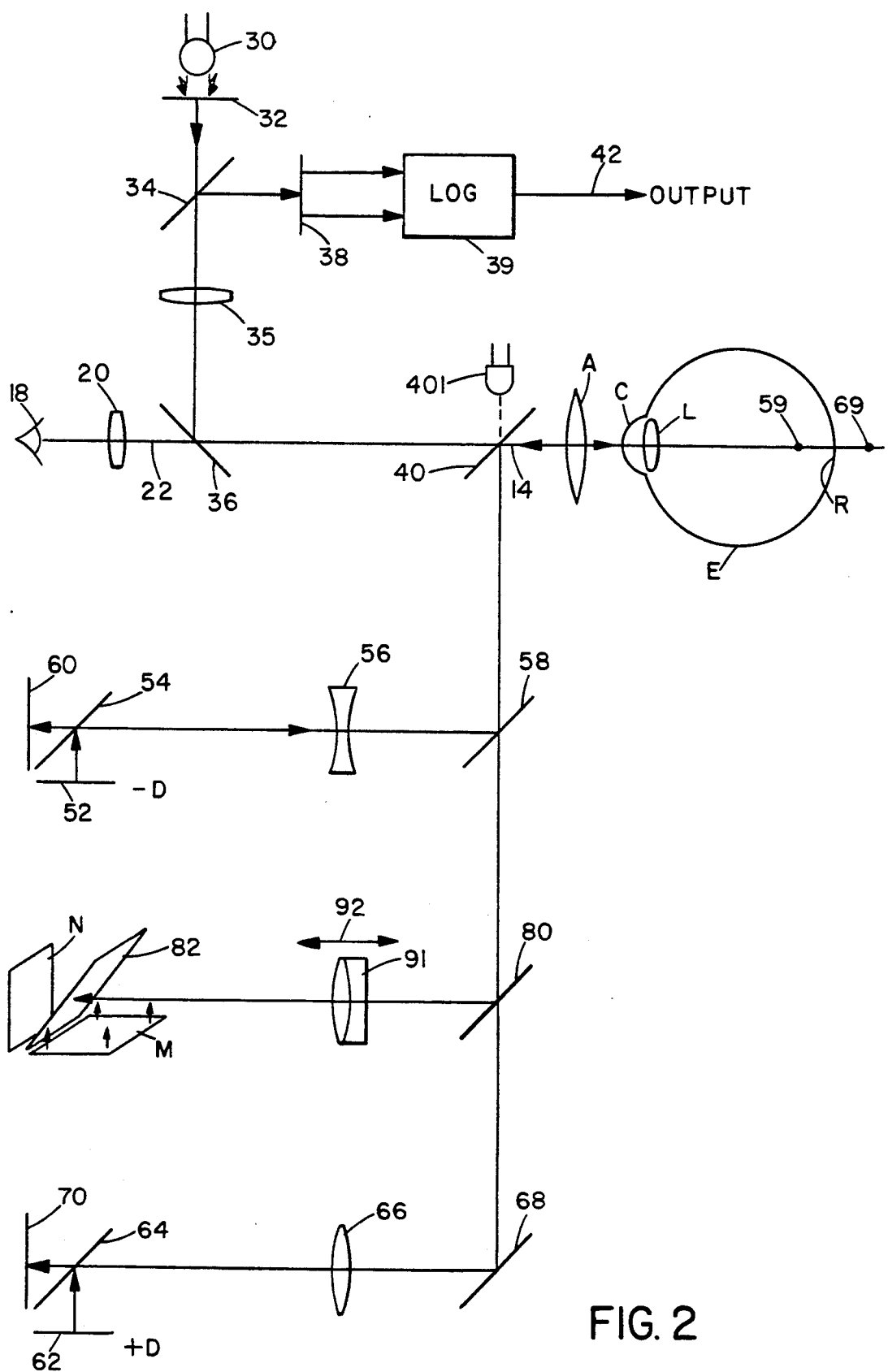
FIG. 2 is an optical schematic of the autorefractor of this invention.

Looking at the schematic of FIG. 2, the optical path of instrument I can be easily understood. In the following discussion, the various light paths of instrument I will be set forth.

First instrument I includes an interrogating eye path 14. This eye path is to and from eye E of patient P (not shown except at eye E in FIG. 2). This interrogating eye path 14 is the route that all light paths to and from the instrument follow between instrument I and patient's eye E.

Secondly, an eye examiner D sight for eye examiner eye 18 is routed through light path 22 to and from patient's eye E. This eye path functions to produce the required gross alignment of instrument I to eye E.

Stopping here, the reader should understand that the disclosed optics and recording electronics are operable when the eye is grossly aligned. However, in the preferred embodiment of this invention, precise eye alignment can be utilized. For such alignment, optics communicated to light source 30 are utilized.

Light source 30 for a conventional Purkinje image is produced at slide 32. Typically, light source 30 is in a discrete color band (for example green) and passes through beam splitter 34, lens 35 and is deflected by beam splitter 36 to interrogating light path 14. Lens 35 functions to focus Purkinje image to cornea C and lens L of eye E. Additionally, visible to the eye examiner is the first Purkinje image, which assists in grossly aligning the instrument with the subject's eye.

Generation of the Purkinje images is conventional. Specifically, these respective images are generated from the surface of the cornea C (most intense image), from the front surface of eye lens L (substantial reduced image), and finally from rear surface of eye lens L (extremely faint image). Light from the respective Purkinje images is retro reflected through hot mirror 40, which is transparent to visible light, and diverted at beam splitters 36 and 34 to detector 38. Detector 38 outputs to log circuit 39 (or similar compression circuit) and finally to output 42.

Use of log circuit 39 can be understood. Specifically, the differences between the various images is several magnitudes. Log circuit 39 mediates this differential. Further, when all signals are aligned, log circuit 39 outputs at 42 a maximum signal—which signal indicates that instrument I at interrogating optical path 14 is correctly aligned to eye E for refraction.

This is an auxiliary Purkinje device and may not be needed. This used at only a close distance to the eye, about 2 to 6 cm range.

Most importantly, the "gross alignment" or "centered" relationship does not require precise alignment. The measurement beam overfills the pupil so that if the eye not perfectly "centered" the patient can still fully see the target, and when the patient looks at the target the optical axis of the instrument and of the patient's eye are "perfectly" aligned.

All that is required is that the patient's eye, appear in the examiner's field of view (through the instrument eyepiece). Because there are many measurement pulses per second, the patient need only momentarily fixate the target to get the refraction. Indication that the eye is aligned, even momentarily, also is signaled by outputs from across Rlim 123 and the outputs of +diopter and −diopter background (diffuse light) amplifiers 102 and 103 shown in FIG. 4. These ouputs are stored and compared for each measurement pulse. Relative differences between these outputs indicate whether the eye is accommodating or not (in accommodation the pupil becomes smaller thereby changing diffuse light from the eye) and whether the eye looking most directly at the fixation target (best alignment means strongest retro reflection of images so that emitter current and output across Rlim is a minimum). The reader should note that the Bruckner Effect which reduces reflected light is not operative in this application, because among other reasons the projected image is a disc rather than a point source.

With the above points in mind, it will be understood that the Purkinje image sensor does not follow the eye, but only indicates when the optical axis of the eye is aligned or nearly aligned (looking at the fixation target) with the instrument's optics.

Purkinje discovered several images reflected from the eye: an image from the cornea (a very strong and completely apparent image), and a second image from the front surface (anterior surface) of the lens, and third image from the posterior surface of the lens. The second and third images are very weak. In the prior art, there has been an inability to use these images to make an electromechanical eye tracker.

This Purkinje image sensor uses a log circuit to make the strong and weak images more nearly equal so that a multiply-segmented photodetector array with associated electronics can determine whether one only segment (indicating coincidence of the three images) has a signal or whether more than one segment (indicating non-coincidence and non-alignment) have signals.

A further application of the Purkinje image sensor is to determine that the patient's eye is within measuring distance and properly in place: When the eye not within distance or not in place, there is no return signal. When there is a return signal (return signal produced at virtually same time as emitted signal) a simple AND logic indicates that an eye is in place and within the power and optics of the instrument.

This third application—vertex range sensor—is in addition to sensing whether alignment and green fixation target (could be red fixation target, use near-infrared to avoid photophobia). The reader will readily appreciate that the output across Rlim 123 can also be used as a vertex sensor: the output being a maximum when the eye is not in place or the vertex is beyond measurement range, and the output of Rlim becoming less as the vertex distance decreases.

Referring again to FIG. 2, a first signal D. is emitted from emitter 52 in the form of a target image for transmission to eye E. This signal passes through negative lens 56 for reflection at beam splitter 58 and then for reflection from hot mirror 40 and through optometer lens "A" onto interrogating eye path 14. Taking the case of an emmetrope, negative image 69 is beyond retinal plane R. Lens "A" acts as a conventional optometer lens to produce converging rays when the image source is at a focal length greater than that of the optometer lens, and diverging rays when the image source less than that of the optometer lens' focal length. The "negative" and "positive" lenses merely shorten the optical path.

The return light path is analogous. Light from image 69 (on the retinal plane R) returns through reflection from the hot mirror 40 and beam splitter 58, and finally passes through beam splitter 54 onto detector 60.

Referring again to FIG. 2, a second signal $D_+$ is emitted from emitter 62 in the form of a target image for transmission to eye E. This signal reflects at beam splitter 64 and passes through positive lens 66 to mirror 68 and then through beam splitters 80, 58 to reflection at hot mirror 40 and onto interrogating eye path 14. Taking the case of an emmetrope, negative image 59 is short of retinal plane R.

The return light path is analogous. Light from image 59 (on the retinal plane R) passes through optometer lens "A" and returns after reflection at the hot mirror 40, passes through beam splitters 58, 80, and reflects from mirror 68, passes through beam splitter 64 and onto detector 70.

Having set forth the light paths, and assuming that the pupil of eye E does not dilate, the intensity of the respective signals can be observed with respect to FIGS. 3A–3F.

Figure 3A:
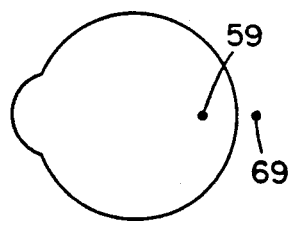
FIGS. 3A, 3C and 3E are schematics of a human eye in cross section illustrating focus of light to the surface of the retinal plane of respective emmetrope, hyperope and myope.
Figure 3C:
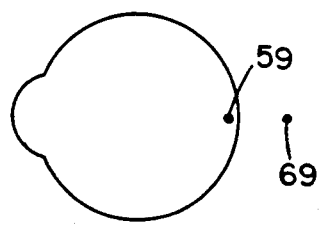
Figure 3E:
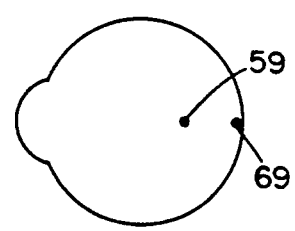
Figure 3B:
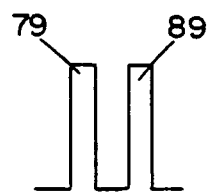
FIGS. 3B, 3D, and 3F are respective schematic signal intensity plots illustrating the operation of the objective refractor of this invention on each of the respective subjects.

Referring to FIGS. 3A and 3B, the case of the emmetrope is illustrated. Presuming that each of the respective light sources is focused with a twenty (20) diopter differential on the eye E of emmetrope for imaging at retinal plane R, it will be seen from FIG. 3B that the respective signals 79 from light source 59 and signal 89 from light source 69 will be approximately equal. This will be because with respect to retinal plane R, images 59, 69 will be approximately equally out of focus.

Figure 3D:
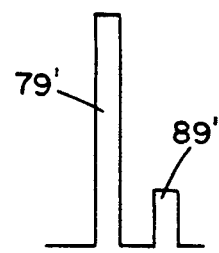

Referring to FIGS. 3C and 3D, the case of a hyperope is illustrated. Presuming that each of the respective light sources is focused with a twenty (20) differential on the eye E of hyperope for imaging at retinal plane R, it will be seen from FIG. 3D that the respective signals 79' from light source 59 is intense. At the same time signal 89' from light source 69 will be diminished. This will be because with respect to retinal plane R, image 69 will be out of focus while image 59 will fall on retinal plane R. This example presumes pronounced hyperopia.

Figure 3F:
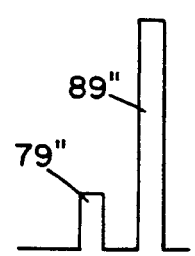

Referring to FIGS. 3E and 3F, the case of a myope is illustrated. Presuming that each of the respective light sources is focused with a twenty (20) diopter differential on the eye E of myope for imaging at retinal plane R, it will be seen from FIG. 3D that the respective signals 79" from light source 59 is diminished. At the same time signal 89" from light source 69 will be intense. This will be because with respect to retinal plane R, image 59 will be out of focus while image 69 will fall on retinal plane R. This example assumes pronounced myopia.

Having set forth the operative examples of FIG. 3A–3F, the problem of outputting a voltage that is proportional to overall sphere can be set forth. The chief problem in producing a ratio between the respective signals is that the eye under examination can dilate. In the case of such dilation, the ratio between the respective images 79, 89 can change. In order to prevent such a change in ratio, the circuitry of FIG. 4 is utilized.

Figure 4:
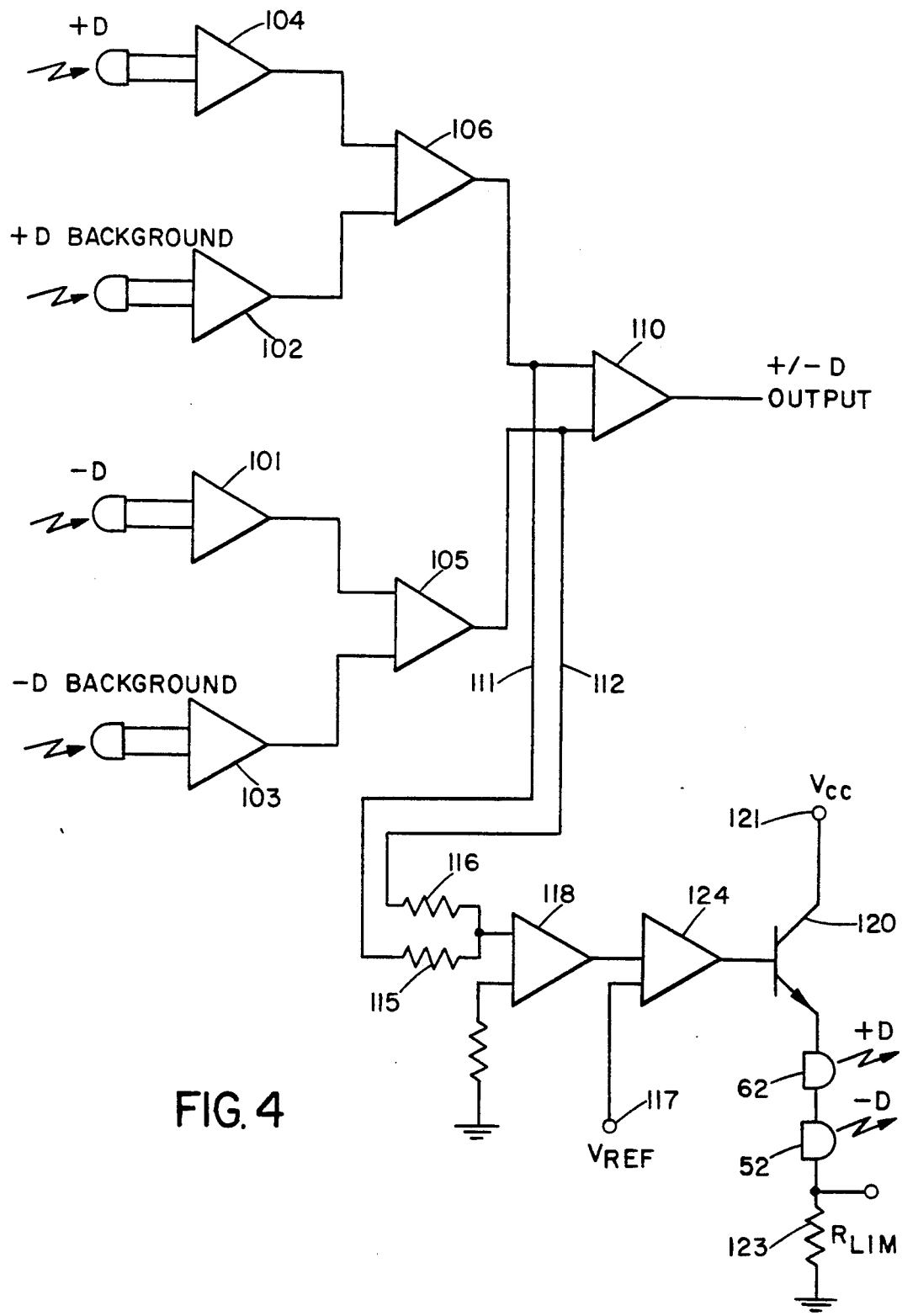
FIG. 4 is a schematic of the differential circuitry useful for determination of gross overall sphere with a constant proportion of signal despite dilation of the examined eye.

Referring to FIG. 4, the first portion of circuitry is conventional. Respective background signals from detectors 60 and 70 and respective image signals from images 59, 69 are routed through amplifiers 101–104 and to summing amplifiers 105, 106. The respective outputs of amplifiers 105, 106 are routed to a differential amplifier 110. Differential amplifier 110 outputs a voltage which is directly proportional to the difference in image intensity. By way of example, a negative voltage can indicate myopia and a positive voltage can indicate hyperopia.

The case of eye E of patient P dilating is set forth in the ancillary circuitry illustrated. Specifically, total signal to comparing amplifier 110 is monitored by respective lines 111, 112. These pass to summing resistors 115, 116 to one input of summing amplifier 118, and the output of summing amplifier 118 goes to the input of current control amplifier 124. The other input of current control amplifier 124 comes from reference voltage input 117. This illustrative current control (clamping) circuit can be replaced by a ratiometric circuit which eliminates the reference voltage, or similar circuit to achieve the same purpose.

Up to now, the ratio of "intensities" of the two detected signals that bracket the emmetrope's retinal focal plane have been considered. The reader should realize that by substituting CCD arrays in place of the discrete photodetectors, and such CCDs being un-apertured, the ratio of the diameters of the detected +diopter image and −diopter image can be used to correlate to refraction. In this case the "normalizing" circuits may or may not be employed.

Using CCD arrays also allows to measure the deformation of the projected disc (or other shape image) to find the axis of deformation and amount of deformation to determine, empirically and using a look-up table, cylinder and axis (astigmatism) of the eye.

Dependent upon total intensity of signal received from both images, output of signal from the current control amplifier 124 goes to the base of transistor 120. Transistor 120 serves to control current from current source 121. Current passes through respective light sources 62, 52 and finally through a limiting resistor 123 and then to ground.

Operation of the circuit with respect to the dilating eye can be understood. Presuming that eye E at the pupil contracts, less signal will be seen at amplifier 124 relative to reference voltage 117. This being the case, the base of transistor 120 will open to permit a greater flow of current through light sources 52, 62. When a greater current flows through the respective light sources 52, 62, the intensity of signal received at amplifier 124 will increase until an equilibrium condition is established. The respective output signal at amplifier 110 will remain essentially in the same ratio and will not be affected by eye dilation.

The reader will understand that the case of pupil contraction is the opposite. The result will remain the same except that total current flow through the respective light sources 52, 62 being reduced. The reader will also understand that numerous other schemes can produce the required normalization of the signal ratios in the presence of eye dilation.

Topographical Mapping of Fundus

More significant than a palm-size auto refractometer may be topographical mapping of the retina. This is possible because different points on the retina can be refracted and refraction correlates to distance to/from the eye's optics, that is, a topological map. By using two wavelengths, say green (red-free light) and red (near-infrared), the surface and sub-surface features of the retina can be mapped. This data could be inputted to a neural network for objective and automatic detection of various eye diseases.

An immediate application in surgery can be locating areas of macular edema. Techniques are being developed for subretinal drainage.

A topological mapping instrument of this nature might help understand the eye better and enable further advances in ophthalmic surgery. Furthermore, sets of data, apparently unrelated, inputted to a neural net, might reveal a method to diagnose incipient glaucoma.

Returning to FIG. 2, the topographical mapping function of this invention can be understood. Specifically, for such mapping, images projected to the fundus must be kept precisely in alignment. Accordingly, use of the Purkinje imaging system is preferred.

Specifically, and referring to FIG. 2, a matrix M of light sources reflects from beam splitter 82, and reflects at beam splitter 80 onto interrogating optical path 14. At interrogating optical path 14, image adjustment of the image of matrix M is made by lens movement of lens 91 towards and away from eye E along path 92. The purpose of a movable lens is merely to allow greater resolution, that is, to map many discrete points: Matrix M must project discrete discs that may be blurred on the retina, but not so blurred that the projected discs on the retina overlap. The topological profile corresponds to the photodetection measurement on the photodetector array N. In the case of obtaining an image of the fundus using a CCD, lens movement enables high resolution of the fundus.

In the preferred embodiment of this invention, the measure aperture overfills the pupil of the eye. In order for accurate measurements to be taken, it is only required that the eye be within the range of the instrument within relative rough limits. These rough limits can be determined by a vertex range sensor.

Vertex Range Sensor

Figure 6A:
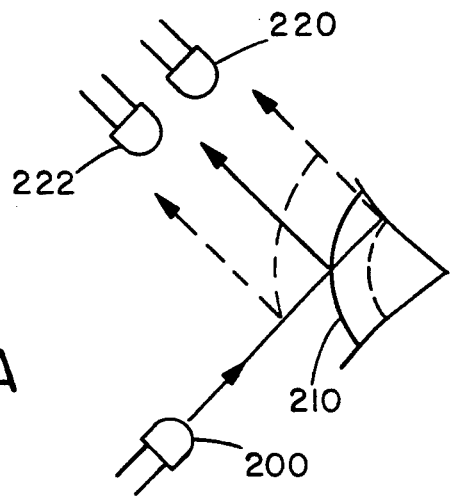
FIG. 6A is an optical schematic and FIG. 6B is an electrical schematic for the vertex sensor of this invention.
Figure 6B:
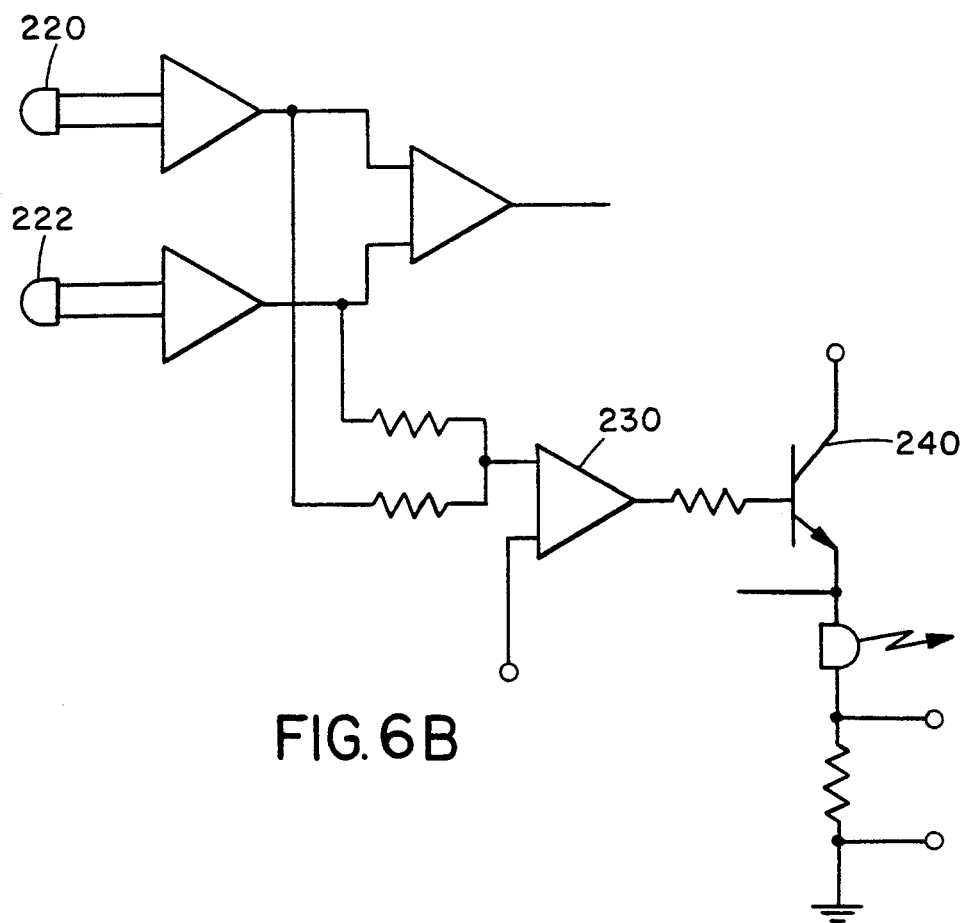

Referring to FIG. 6A, a single emitter 200 (IR) projects a beam onto the eye's cornea 210 as shown. This is essentially the same as a number of other similar devices for finding distance. The main difference in this arrangement is the electronics of FIG. 6B: the two inputs 220, 222 (photodetector signals) are summed together at amplifier 230 and the emitter current 240 increases or decreases to maintain a constant sum of the two inputs. This means that the resulting voltage from the detectors' electronics is proportional to vertex distance. And this voltage can be used to make corrections in diopter measurement caused by varying eye distances from the instrument optometer lens, if such correction be required.

The eye, however, and this arrangement of +D and −D signals will be understood to make the eye measurement rather insensitive to changes in vertex distance.

Assuming correct alignment of instrument I at interrogating optical path 14 to eye E, the auto refraction can now occur. In explaining the requisite auto refraction, the case of an emmetrope will first be considered. Thereafter, and with reference to FIGS. 3A–3F, the reception of signals from the eye will be set forth. Finally, and with reference to FIG. 4, a circuit for outputting a voltage proportional to prescription at the eye E is set forth.

Figure 5B:
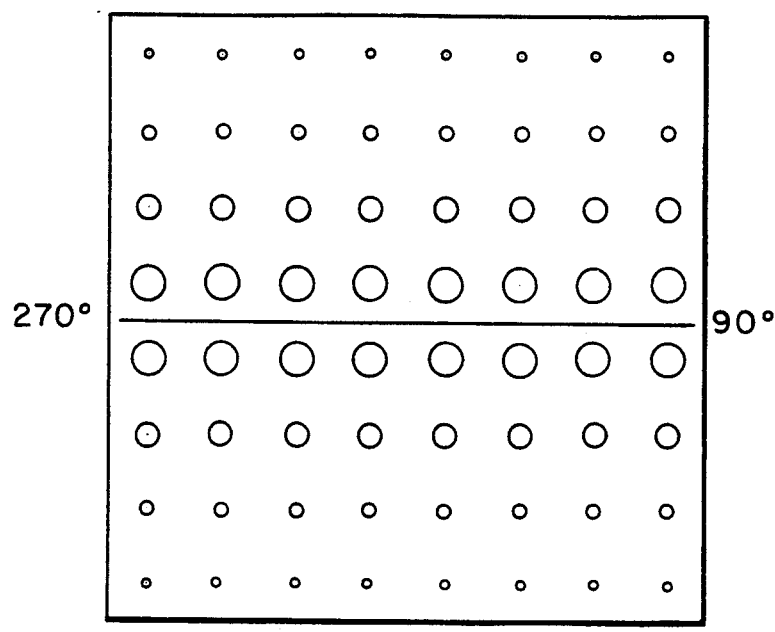
FIG. 5B is an intensity diagram of the eye where a patient has astigmatism along a 90 degree axis, the astigmatism here being illustrated in the range of positive one half of a diopter.
Figure 5A:
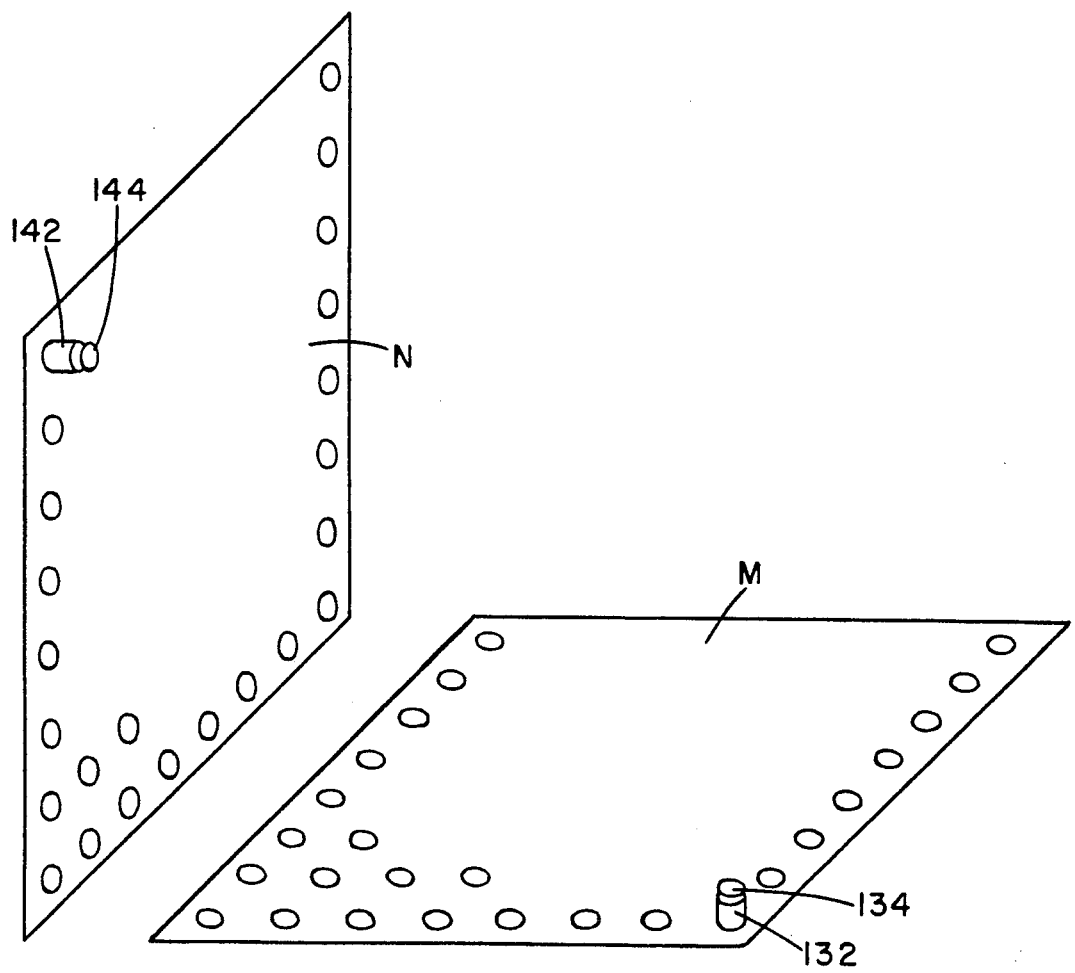
FIG. 5A is a schematic for the projection of an image registered to the eye.

Referring to FIGS. 5A, image matrix can be understood. As there illustrated, matrix M includes an 8 by 8 light source array—such as low-intensity microlasers 132 passing through corresponding micro lenses 134. These respective light sources 132 and lenses 134 are given respective focal lengths so that the matrix of light sources projects to retinal plane R on eye E.

The received image is analogous. Respective detector segments 142 receive through corresponding micro lenses 144 images from retinal plane R of eye E. The respective projecting matrix M and receiving array N are registered, one to another. In this way an element of receiving array N overlies a corresponding element of projecting matrix M.

Referring to FIG. 5B, the respective results of such an image are projected. Specifically, it will be remembered that the spherical portion of this invention observes gross sphere only; thus far astigmatism has been ignored.

Referring to FIG. 5B, the resultant image received at array N is shown projected—as at a conventional CRT. Amplification of the respective matrix locations is shown graphically in increased size at each matrix position. This being the case, it can be seen that the patient P includes positive sphere along the indicated 90° axis.

Mean Sphere error and ±diopter error is obtained from the main diopter measuring circuits, cylinder and axis are obtained by one of three methods.

The first method is by using a fixed detector array (microlenses and photodetectors) to find meridional refraction (points around the optical axis) and these refractive measurements used in either Lawrence's formula (remembering that ±diopter sphere is already given: Immediately finding ±diopter sphere is a significant difference compared to conventional meridional refractometry), or using a curve fitting program to find the best curve to correct for astigmatism. In theory, this method can perfectly correct for astigmatism, even irregular astigmatism, because the resulting corrective lens could be computer-ground to perfectly match all the various meridional refractive measurements on the microlens detector array.

A second method is measuring the elliptical distortion of the projected circular disc. The amount and direction of the elliptical distortion correlates to meridional refraction and provides at least three axes to plug into Lawrence's formula, or remembering that ±D sphere already found, a curve fitting program to give cylinder and axis.

A third method detects the distortion of a retro reflected circular pattern and measures the orientation of distortion to find axis, and measures ratio of length-to-width and then uses a simple look-up table to find cylinder.

The reader will understand that here I illustrate only the illumination pattern of a matrix. It will be apparent that other techniques can be utilized. For example, elliptical distortion might be detected by an array of meridional photodetectors located at the −D photodetector position. The important concept is that operation of my preferred refractor, I use first the determination of gross sphere and thereafter—knowing the gross sphere—examine for cylinder and axis.

Having set forth the preferred embodiment of this invention, it can be seen that with respect to the pulse techniques, optics, and measurement protocol, numerous advantages are realized. These include:

1. Pulse Techniques a) Very short pulses, less than one millisecond, stop the motion of the eye.

b) Many measurements, 100 or more, taken every second so that "valid" measurements are averaged into the final refraction, but non-aligned and other spurious measurements eliminated.

c) Random noise reduced by the square root of the number of valid measurements, that is, if 49 valid measurements, the signal-to-noise ratio is improved by seven times.

d) Low average power yet high peak optical power output, e.g., if a component is rated at 1 milliwatt but has a duty cycle of 20%, the peak power could be increased five times to 5 milliwatts.

e) Because of low average power and high peak output, tiny components can be used in the instrument. To increase power rating and for longer life, heat sinks can be employed. In any case, the instrument for each patient will be used only for a few seconds.

f) Low power consumption enables an entirely self-contained, battery-powered instrument.

g) Small size of the instrument means palm-size and entirely self-contained. The instrument casing can be injected molded in two halves with the optical and electronic components fitting into pre-formed mounts. Equally important, however, is lower cost of manufacture (smaller and fewer components), lower distribution cost (ship by mail), and lower service costs (replace instrument via express mail).

2. Non-Critical Optics a) Measurement beam overfills the pupil.

b) Fixed optical system with no moving parts.

c) Full refraction determined by single measurement pulse.

d) Photodetectors have high quantum efficiency and are lensed for high sensitivity.

e) Optical and electronic filters suppress ambient light.

f) Dichroic beam splitters increase efficiency of light path.

g) Relatively high optical output of LED measurement beam increases signal strength (less, however, than a standard ophthalmoscope so that use is entirely safe).

h) Very sensitive photodetector amplifier with input bias around 1 pA or less, and stability in microvolts.

g) Internal instrument light ("glare") suppressed by optical and electronic means.

3. Extensive Signal Processing a) so that under changing signal strength (pupil dilating/contracting, retinal pigmentation, etc.) the two main diopter measuring signals must remain constant because the ratio of these two signals correlates to refraction. (In the case of CCD photodetectors, the ratios of the blur circles are used as previously described.)

1) (Signal of +D emitter)+(Signal of −D emitter)=constant (fixed) voltage; or, 2) (Signal of +D emitter)=(Signal of −D emitter) and (Sign +D emitter)=Sign −D emitter)=constant (fixed) voltage The "constant (fixed) voltage" can be set at, say, 5 V, or any other voltage that satisfies the circuitry and formula 1) or 2).

b) Background noise (diffuse light) is subtracted from the main diopter signals.

1) off-axis photodiodes detect the diffuse light.

2) diffuse light can be from internal reflections of the eye and from the iris, more or less diffuse light could indicate changing (accommodative) pupil conditions.

3) Instrument glare suppressed optically, but with output from across the R limiter of the diodes this glare can be subtracted (eliminated) from the main diopter signals because with higher (lesser) signal output and more (less) glare the R limiter voltage will be higher (lesser).

c) Vertex range makes the instrument automatic for close (or one meter) measurements: The instrument will not start producing measurement pulses unless the instrument is within proper vertex distance. This circuit is different from other similar appearing circuits because a voltage that corresponds to vertex distance is produced, and this voltage can be used for minor corrections in the refractive readings.

e) Diffuse light levels change to indicate maximum iris opening and closure to indicate minimum accommodation (the pupil becomes smaller upon accommodation).

f) Purkinje image sensor detects when the first and second images (from a separate, visible green LED) are coincident. This is an auxiliary sensor for close-up refraction and may used where required.

h) Data storage records all the "valid" measurements.

i) By using the signals 1) generated across $R_{lim}$ of the emitters and 2) background (diffuse) light detectors, alignment/minimal accommodation can be determined because 1) voltage across $R_{lim}$ is at a minimum when the eye is unaccommodated (accommodation causes the pupil of the eye to contract when the ciliary body pulls on the lens to shorten the lens' focal length).

Figure 7A:
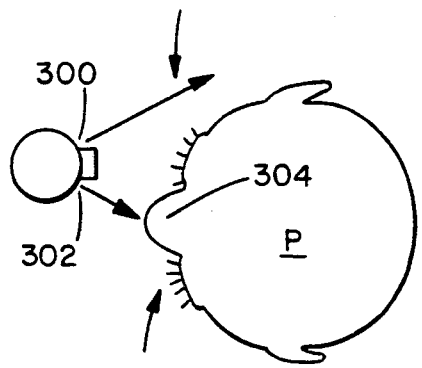
FIG. 7A is a plan view of a patient utilizing left and right eye sensors shown sampling the face of the patient during examination of the right eye of the patient.
Figure 7B:
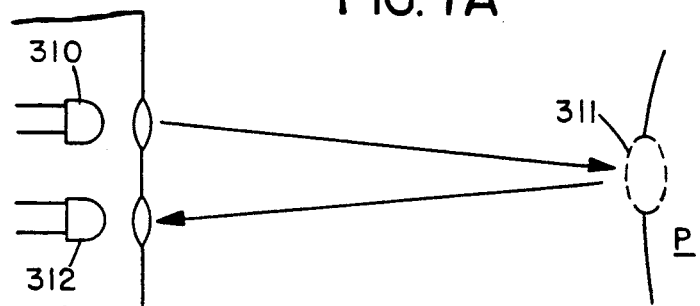
FIG. 7B is an expanded side elevation section of a light source and sensor; and, FIG. 7C is a circuit for comparing the respective views of the patients face for indicating the particular eye of the patient examined as well as the general proximity of the instrument to a patient.
Figure 7C:
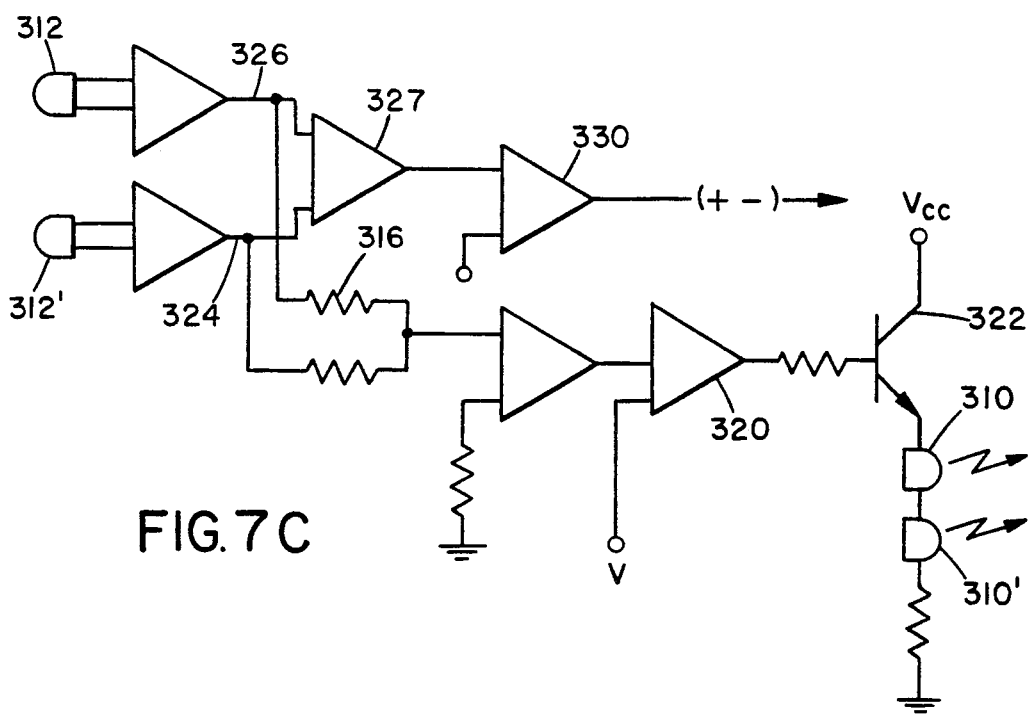

Referring to FIGS. 7A-7C, an embodiment of the refractor is set forth in which the eye of a patient is indicated—left or right—during the examination of a patient P. This device enables the particular measurement to be correlated with the eye examined and enables comparison to a corresponding measurement of the other eye. It is particularly useful in identifying amblyopia.

Referring to FIG. 7A, emitter/receptor pair 300 sends out a signal that is not reflected during examination of the eye of a patient P. Emitter/receptor pair 302 sends out a signal that is reflected during examination of the eye of a patient P.

Referring to FIG. 7B, one of the emitter/receptor pairs 300, 302 is illustrated. An emitter 310 projects a beam 311 on the nose of patient P. A return signal is registered at receptor 312.

Referring to FIG. 7C, photosensors 312 for left eye and 312' for the right eye are illustrated. Outputs 324, 326 are routed to summing resistors 316 and thereafter to amplifier 320. Dependent upon the strength of signal received, transistor 322 passes current through respective light sources 310 for the right eye and 310' for the left eye. Where signal is faint, the respective light sources 310, 310' operate at full intensity. Where the signal is strong, output through amplifier 320 is reduced and current through respective light sources 310, 310' is reduced.

Determination of the particular eye being examined will be made through comparison amplifier 327. Where left eye 312 sensor has the predominating signal, a positive voltage will be output through amplifiers 327, 330. Where right eye 312' sensor has the predominating signal, a negative voltage will be output through amplifiers 327, 330. Thus, by the polarity of the signal utilized, determination of the particular eye examined can be made. By coupling the polarity of the signal to the measurement taken, measurements of each eye can be tagged and examined for disparities evidencing amblyopia.

It will be noted that because the circuit is comparative, whether a person of dark or light pigmented skin is examined is of no matter. Presuming that the respective detectors are in gross range of a patient and pass the respective preset thresh holds of amplifiers 320, 330, a signal indicating left or right eye examination will be emitted from amplifier 330.

Subsequently, refractive measurements can be categorized as to right eye and left eye. When the refractive readings are sufficiently disparate or when both refractive readings indicate poor eyesight, the instrument alerts the eye examiner to further examine the patient for possible amblyopia.

Provision is made for auto calibration of the instrument at the beginning of each measurement sequence to ensure extreme linearity and zero-drift long term stability. The reader will understand that auto calibration can be obtained in a variety of ways and that this method is illustrative and not all inclusive.

Referring to FIG. 2, Photodetector 401 is located in the path of −diopter emitter 52 and +diopter emitter 62. The location of 401 could also be at beamsplitter 58 or other similarly postioned location. Because hot mirror 40 "leaks," or can be designed to leak 1% or so of the emitter beam, photodetector 401 can measure optical output from the −diopter and +diopter emitters.

In brief, a series of calibrated pulses alternately pass through each emitter so that either a correction factor can be applied to one or both emitters to make the optical outputs equal for a given calibrated emitter current or a correction factor can be incorporated in signal processing of the detected retro reflected signals. A particular advantage of this method—beyond enabling extreme linearity and zero-drift stability—is to provide more "calibration marks" at the extreme ranges of the diopter scale for greater accuracy.

What is claimed is:

1. An autorefractor for determining the departure in gross sphere for the eye of a refracted patient from an emmetropia prescription comprising in combination:

an optical path for interrogating an eye for prescription, said eye having a retina, a cornea and a lens;

first means for projecting a first image along said optical path to the retina of said eye having a gross sphere with a preselected positive dioptric value relative to said emmetropia prescription;

first detector means for receiving said first image from said optical path reflected from the retina of said eye and generating a first signal proportional to an intensity of said first image;

second means for projecting a second image to said optical path to the retina of said eye having a gross sphere with a preselected negative dioptric value relative to said emmetropia prescription;

second detector means for receiving said second image from said optical path reflected from the retina of said eye and generating a second signal proportional to an intensity of said second image; and comparison means for receiving said first and second signals for indicating a relative intensity of said first and second images and generating a signal proportional to the gross sphere of said eye.

2. The autorefractor of claim 1 further comprising:

means for projecting an image array along said optical path to the retina of said eye with a preselected dioptric value relative to said emmetropia prescription;

means for receiving said image array from said optical path from the retina of said eye; and means for displaying a relative intensity across said image for determining axis of power astigmatism of said eye.

3. The autorefractor of claim 1 and including:

means for normalizing said first and second detector means against dilation of said eye.

4. The autorefractor of claim 1 and including:

an optical sight path aligned to said optical path for grossly aligning said detector to said eye.

5. The autorefractor of claim 4 further comprising:

means for projecting a Purkinje image along said optical path focused to the vicinity of the cornea of said eye;

detector means for receiving a plurality of reflected Purkinje images at least from the cornea of said eye and from a refracting surface of the lens of said eye; and means for monitoring a maximum intensity of said plurality of reflected Purkinje images whereby alignment of said instrument to said eye is signaled.

6. The autorefractor of claim 5 wherein said means for monitoring a maximum intensity of said plurality of reflected Purkinje images includes a log circuit for comparison of intensity of said plurality of reflected Purkinje images.

7. The autorefractor of claim 1 further comprising two light sources for projecting $+D$ and $-D$ images; and CCD photodetectors for measuring blur circles and ratios of diameters of such circles along with deformation to obtain refractive error.

8. The autorefractor of claim 1 further comprising means for determining best alignment and minimal accommodation responsive to signals across an emitter $R_{lim}$ and a background light photodetector.

9. A process for autorefracting an eye for determining the departure in gross sphere of a refracted patient from an emmetropia prescription wherein the eye has a lens, a cornea and a retina, the process comprising in combination:

providing an optical path for interrogating the eye for prescription;

projecting a first image along said optical path to the retina of said eye with a gross sphere with a preselected positive dioptric value relative to said emmetropia prescription;

detecting said first image from said optical path reflected from the retina of said eye and generating a first signal proportional to an intensity of said first image;

projecting a second image along said optical path to the retina of said eye with a gross sphere with a preselected negative dioptric value relative to said emmetropia prescription;

detecting said second image from said optical path reflected from the retina of the eye and generating a second signal proportional to an intensity of said second image; and comparing said first and second signals for indicating a relative intensity of said first and second image to determine overall gross sphere of said eye.

10. The process of autorefracting of claim 9 and including the steps of:

projecting an image array comprising a third image along said optical path to the retina of said eye with a preselected dioptric value relative to said emmetropia prescription;

receiving said third image reflected from said optical path from the retain of said eye; and displaying the relative intensity within said third image for determining axis of power of astigmatism of said eye.

11. The process of autorefracting of claim 9 and including the steps of:

providing an optical sight path aligned to said optical path for grossly aligning said detector to said eye of said patient; and, aligning said instrument to the eye of said patient.

12. The process of autorefracting of claim 11 and including the steps of:

projecting a Purkinje image along said optical path focused in a vicinity of the cornea of said eye;

receiving a plurality of reflected Purkinje images at least from the cornea of said eye and from a refracting surface of the lens of said eye; and monitoring the maximum intensity of said plurality of reflected Purkinje images whereby alignment of said instrument to said eye is signaled.

13. The process of autorefracting of claim 12 wherein the step of monitoring the maximum intensity of said plurality of Purkinje images includes logarithmically comparing said plurality of reflected Purkinje images.

14. The process of autorefracting of claim 9 further comprising:

normalizing said first and second detector means against dilation of said eye of said patient.

* * * * *

UNITED STATES PATENT AND TRADEMARK OFFICE
CERTIFICATE OF CORRECTION

PATENT NO. : 5,329,322
DATED : July 12, 1994
INVENTOR(S) : Don R. Yancey

It is certified that error appears in the above-indentified patent and that said Letters Patent is hereby corrected as shown below:

Column 16, line 13, "retain" should read --retina--.

Signed and Sealed this

Third Day of January, 1995

Attest:

BRUCE LEHMAN

*Attesting Officer*      *Commissioner of Patents and Trademarks*